(12) United States Patent
Liu et al.

(10) Patent No.: US 11,609,168 B2
(45) Date of Patent: Mar. 21, 2023

(54) AUTOMATIC TEST SYSTEM AND METHOD FOR MECHANICAL PARAMETERS OF SURROUNDING ROCK APPLICABLE TO TBM

(71) Applicant: SHANDONG UNIVERSITY, Shandong (CN)

(72) Inventors: Bin Liu, Shandong (CN); Ruirui Wang, Shandong (CN); Boyang Gao, Shandong (CN); Xu Guo, Shandong (CN); Yaxu Wang, Shandong (CN); Guangzu Zhao, Shandong (CN); Yan Zhu, Shandong (CN); Bin Wang, Shandong (CN)

(73) Assignee: SHANDONG UNIVERSITY, Jinan (CN)

( * ) Notice: Subject to any disclaimer, the term of this patent is extended or adjusted under 35 U.S.C. 154(b) by 99 days.

(21) Appl. No.: 17/430,081

(22) PCT Filed: Oct. 14, 2020

(86) PCT No.: PCT/CN2020/120952
§ 371 (c)(1),
(2) Date: Aug. 11, 2021

(87) PCT Pub. No.: WO2021/073542
PCT Pub. Date: Apr. 22, 2021

(65) Prior Publication Data
US 2022/0146389 A1 May 12, 2022

(30) Foreign Application Priority Data

Oct. 15, 2019 (CN) .......................... 201910979186.2

(51) Int. Cl.
*G01N 3/56* (2006.01)
*B25J 19/02* (2006.01)
(Continued)

(52) U.S. Cl.
CPC ................ *G01N 3/56* (2013.01); *B25J 19/02* (2013.01); *G01B 11/24* (2013.01); *G01N 3/06* (2013.01);
(Continued)

(58) Field of Classification Search
CPC .. G01N 3/56; G01N 3/06; G01N 3/10; G01N 3/24; G01N 33/24; G01N 35/0099;
(Continued)

(56) References Cited

FOREIGN PATENT DOCUMENTS

| CN | 101008597 A | 8/2007 |
|----|-------------|--------|
| CN | 103969139 A | 8/2014 |

(Continued)

OTHER PUBLICATIONS

Mar. 27, 2020 Office Action issued in Chinese Patent Application No. 201910979186.2.
(Continued)

*Primary Examiner* — Jonathan M Dunlap
(74) *Attorney, Agent, or Firm* — Oliff PLC

(57) ABSTRACT

An automatic test system and method for mechanical parameters of surrounding rock applicable to a TBM. The system includes: an aggregate portion collecting a rock slag in a TBM tunneling process in real time; a gripping portion gripping any rock slag from obtained rock slags; a visual processing apparatus performing three-dimensional imaging for a rock slag under test in an infrared ranging manner; calculating positions of loading points for an abrasiveness test experiment, and determining, based on a spacing between loading points, whether rock slag under test meets a requirement; and determining actual positions of loading points if the rock slag under test meets the requirement, and determining a region, on a surface of rock slag, that meets a set condition as an action region for abrasiveness test experiment; and a rock abrasiveness test apparatus automati-
(Continued)

cally performing an abrasiveness test for a rock slag under test that meets a requirement.

13 Claims, 3 Drawing Sheets

(51) Int. Cl.
*G01B 11/24* (2006.01)
*G01N 3/06* (2006.01)
*G01N 3/10* (2006.01)
*G01N 33/24* (2006.01)
*G01N 35/00* (2006.01)
*B25J 9/16* (2006.01)

(52) U.S. Cl.
CPC ............... *G01N 3/10* (2013.01); *G01N 33/24* (2013.01); *G01N 35/0099* (2013.01); *B25J 9/1682* (2013.01); *G01N 2203/0048* (2013.01); *G01N 2203/0676* (2013.01)

(58) Field of Classification Search
CPC ..... G01N 2203/0048; G01N 2203/0676; B25J 19/02; B25J 9/1682; G01B 11/24
See application file for complete search history.

(56) References Cited

FOREIGN PATENT DOCUMENTS

| CN | 205808346 U | | 12/2016 | |
|---|---|---|---|---|
| CN | 107780446 A | | 3/2018 | |
| CN | 108253938 A | | 7/2018 | |
| CN | 208206712 U | | 12/2018 | |
| CN | 109443917 A | | 3/2019 | |
| CN | 109443946 A | | 3/2019 | |
| CN | 110043267 A | | 7/2019 | |
| CN | 110308167 A | | 10/2019 | |
| CN | 110646307 A | * | 1/2020 | |
| CN | 110823737 A | | 2/2020 | |
| JP | 2013-160660 A | | 8/2013 | |
| RU | 187993 U1 | * | 3/2019 | ............... B24D 3/00 |
| WO | 2009/070365 A1 | | 6/2009 | |

OTHER PUBLICATIONS

Mar. 27, 2020 Search Report issued in Chinese Patent Application No. 2019109791862.
Feb. 4, 2021 International Search Report issued in International Patent Application No. PCT/CN2020/120952.
Jan. 19, 2021 Written Opinion issued in International Patent Application No. PCT/CN2020/120952.

* cited by examiner

AUTOMATIC TEST SYSTEM AND METHOD FOR MECHANICAL PARAMETERS OF SURROUNDING ROCK APPLICABLE TO TBM

BACKGROUND

Technical Field

The present invention relates to the technical field of tests for mechanical parameters of surrounding rock, and in particular, to an automatic test system and method for mechanical parameters of surrounding rock applicable to a TBM.

Related Art

The description in this section merely provides background information related to the present invention and does not necessarily constitute the prior art.

The TBM method is a mainstream method for performing construction on deep and long tunnels, and has advantages of high tunneling speed, low construction costs, small construction disturbance, being economical and safe, and the like during construction. However, TBM construction is extremely sensitive to rock mass conditions, and parameters such as a uniaxial compressive strength and an abrasiveness index (CAI) of surrounding rock greatly affect construction efficiency and costs of a TBM. In a construction section with a relatively high surrounding rock strength, a load required by the TBM for rock breaking increases, causing an increase in the degree of difficulty in rock breaking and a decrease in the tunneling efficiency. Moreover, in a section with a low surrounding rock strength and poor stability, although the tunneling speed of the TBM is high, a significantly long downtime for supporting is required, and consequently the tunneling efficiency is still relatively low. In addition, based on statistics, time and costs for replacing cutters caused by abrasion occupy more than one third of tunnel construction costs of the TBM. In the cutter abrasion aspect, the abrasiveness index (CAI) is one of parameters that play a vital role. Therefore, obtaining a compressive strength and an abrasiveness index of surrounding rock in real time is of great significance to determining TBM tunneling efficiency and cutter costs, whereby tunneling control parameters and a construction solution are adjusted.

Currently, there is no method for obtaining rock mass parameters in real time in an aspect of obtaining strength parameters of surrounding rock on which TBM performs construction, and in a mainstream manner, coring needs to be performed on site, and a rock is cut and polished into a standard rock mass sample, and then a uniaxial compress test and an abrasiveness test for a rock are performed indoor to obtain a compressive strength and an abrasiveness index of the rock. The method has the following problems:

1. In a TBM environment, a downtime and maintenance time is needed for coring work, and consequently affecting tunneling.

2. Processes of drilling for core, processing, and testing is time-consuming, and obtained rock mass parameters lack in timeliness, thereby failing in meeting actual requirements on timeliness and real-time performance for parameters such as a compressive strength and an abrasiveness index of rock mass by TBM tunneling.

An industrial robot used in assembly line operations can accurately grip and process a product part on an assembly line, which provides a good concept for a real-time rock mass parameter test for TBM tunneling. A rock slag produced in a TBM tunneling and rock breaking process is conveyed out of a cave along with a belt conveyor, which has relatively high similarity with a product assembly line used in industrial production. In addition, the rock slag produced during TBM rock breaking can reflect rock mass conditions of a current construction surface in real time, which is a "natural sample" for a rock mass parameter test, and is also an important reference for adjustment of a solution for tunneling and construction by the TBM. Therefore, gripping a rock slag in real time by using an industrial robot and performing a test is a feasible method for obtaining rock mass parameters in real time. However, applying a robot to perform an automatic test has the following difficulties:

1. A speed of the belt conveyor of the TBM is relatively high, and how to quickly and accurately grip a rock slag that meets a test requirement?

2. How to capture size and shape information of a rock slag through computer vision and determine whether the rock slag meets a test requirement?

3. How to perceive a position for gripping a rock slag, and determine a contact state between the rock slag and a test platform?

4. How to automatically adjust a position and an angle for gripping a rock slag upward, so that the rock slag meets a requirement for a sample posture for a compress and abrasiveness test?

5. How to automatically perform loading and unloading, and perform a compressive strength and abrasiveness index test by the test platform?

6. The abrasiveness index test for a rock requires high test precision, and how to complete a high-precision test in a strong vibration environment of TBM tunneling?

SUMMARY

To resolve the problem described above, the present invention provides an automatic test system and method for mechanical parameters of surrounding rock applicable to a TBM, to perform a test by using an irregular rock slag obtained through dynamic excavation by a TBM as a sample, thereby implementing automatically testing abrasiveness and strength parameters of surrounding rock online in real time.

In some implementations, the following technical solutions are used:

An automatic test system for mechanical parameters of surrounding rock applicable to a TBM is provided, including:

an aggregate portion, capable of collecting a rock slag in a TBM tunneling process in real time;

a gripping portion, capable of gripping any rock slag from obtained rock slags;

a visual processing apparatus, capable of: performing three-dimensional imaging for a rock slag under test in an infrared ranging manner; calculating positions of loading points for an abrasiveness test experiment, and determining, based on a spacing between the loading points, whether the rock slag under test meets a requirement; and determining actual positions of the loading points if the rock slag under test meets the requirement, and determining a region, on a surface of the rock slag, that meets a set condition as an action region for the abrasiveness test experiment; and a rock abrasiveness test apparatus, capable of automatically performing an abrasiveness test for a rock slag under test that meets a requirement.

By shoveling a rock slag by using a mechanical bucket, a rock slag gripping process is decomposed into two steps of shoveling the rock slag, making the rock slag enter the bucket through movement of the rock slag, and then clamping the rock slag by using a mechanical clamp, thereby changing clamping a dynamic rock slag to clamping a static rock slag on the bucket; and a problem that in a case that a rock slag on the belt conveyor of the TBM moves at a high speed, it is difficult for a common mechanical clamp to directly clamp the dynamic target moving at a high speed is resolved.

Positions of loading points are automatically located by using a three-dimensional shape model of the rock slag, and whether the rock slag meets a requirement is determined, thereby ensuring the real-time accuracy and authority of an abrasiveness test experiment and an online compressive strength test for the rock slag that are performed in the present invention.

In some other implementations, the following technical solution is used:

An automatic test method for mechanical parameters of surrounding rock applicable to a TBM is provided, including:

obtaining a rock slag in a TBM tunneling process as a rock slag under test;

determining a three-dimensional shape model of the rock slag in an infrared ranging manner;

calculating positions of loading points by using the three-dimensional shape model of the rock slag, and determining, based on a spacing between the loading points, whether the rock slag under test meets a requirement;

determining actual positions of the loading points if the rock slag under test meets the requirement, and selecting a region, on a surface of the rock slag, that meets a set condition as an action region for an abrasiveness test experiment, to perform an abrasiveness test; otherwise, reselecting a rock slag; and moving the rock slag under test to a set position for a compressive strength test after the abrasiveness test.

Compared with the prior art, the present invention has the following beneficial effects:

In the test system for mechanical parameters of surrounding rock carried in a TBM provided in the present invention, an excavated rock slag conveyed on a belt conveyor is gripped by using a robot to perform an abrasiveness experiment and a compressive strength experiment on site. Compared with the existing manual drilling for core and indoor testing methods with extremely poor timeliness, the automatic test method for mechanical parameters of surrounding rock applicable to a TBM provided in the present invention has advantages such as high timeliness, a high degree of automation, and being safe and economical, thereby effectively resolving a problem that it is difficult to obtain strength information of surrounding rock on which a TBM performs construction currently in real time, and providing real-time surrounding rock condition information and a control parameter decision basis for TBM tunneling.

In the present invention, a rock slag is shoveled by using a mechanical bucket, thereby resolving a problem that in a case that a rock slag on the belt conveyor of the TBM moves at a high speed, it is difficult for a common mechanical clamp to directly clamp the dynamic target moving at a high speed. A rock slag gripping process is decomposed into two steps of shoveling a rock slag, making the rock slag enter the bucket through movement of the rock slag, and then clamping the rock slag by using the mechanical clamp, thereby changing clamping a dynamic rock slag to clamping a static rock slag on the bucket.

In the present invention, positions of loading points are automatically located by using a three-dimensional shape model of the rock slag, and whether the rock slag meets a requirement is determined, thereby ensuring the accuracy and authority of an abrasiveness test experiment and an online compressive strength test for the rock slag that are performed in the present invention.

In the invention, the rock slag is flushed by using a high-pressure sprinkler disposed on a mechanical arm of the clamp. Therefore, on one hand, floating dust on a surface of a rock slag produced during excavation can be cleaned, to prevent dust from decreasing friction on the surface of the rock slag and causing an error in the subsequent compressive strength test; on the other hand, flushing the rock slag can also improve saturation of the rock slag, thereby avoiding a compressive strength result difference caused by different natural water contents of rock slags.

BRIEF DESCRIPTION OF THE DRAWINGS

The accompanying drawings constituting a part of this application are used for providing further understanding for this application. Exemplary embodiments of this application and descriptions thereof are used for explaining this application and do not constitute any inappropriate limitation to this application.

1. Aggregate apparatus; 2. Mechanical gripper; 3. Infrared depth binocular camera; 4. Rock abrasiveness test platform; 5. Compressive strength test platform; 6. Rock slag; 7. Belt conveyor; 8. Bucket; 9. High-pressure sprinkler; 10. Test platform support; 11. Electric hydraulic telescopic oil cylinder; 12. Steel pin; 13. CCD microscope camera; 14. Rock fixture; 15. Pin supply circular disk; 16. Abradant steel pin collecting box; 17. Vibration damping base; 18. Loading cone; 19. Electric hydraulic jack; 20. Program-controlled host.

DETAILED DESCRIPTION

It should be noted that the following detailed descriptions are all exemplary and are intended to provide a further understanding of this application. Unless otherwise specified, all technical and scientific terms used in the present invention have the same meaning as commonly understood by a person of ordinary skill in the art to which this application belongs.

It should be noted that terms used herein are only for describing specific implementations and are not intended to limit exemplary implementations according to this application. As used herein, the singular form is intended to include the plural form, unless the context clearly indicates otherwise. In addition, it should further be understood that terms "comprise" and/or "include" used in this specification indicate that there are features, steps, operations, devices, components, and/or combinations thereof.

Embodiment 1

Figure 1:
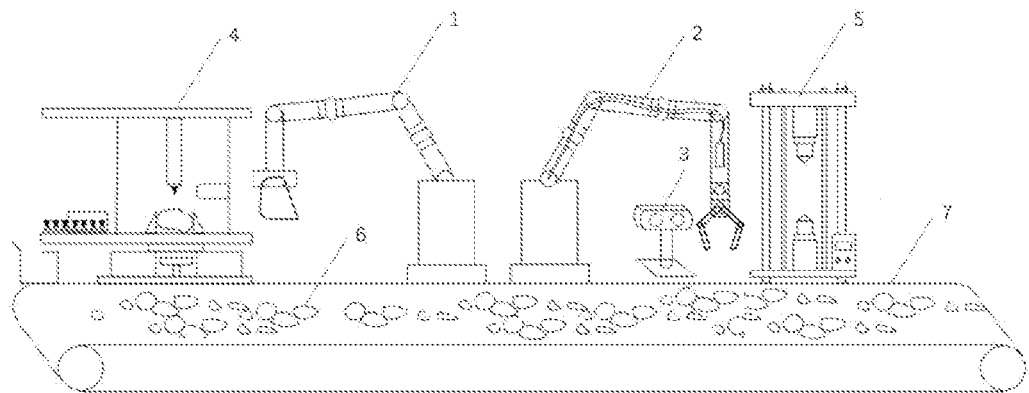
FIG. 1 is a front view of an automatic test system for mechanical parameters of surrounding rock applicable to a TBM according to Embodiment 1 of the present invention.

In one or more embodiments, an automatic test system for mechanical parameters of surrounding rock applicable to a TBM is disclosed. Referring to FIG. 1, the system includes: an aggregate apparatus 1, a mechanical gripper 2, a high-pressure sprinkler 9, an infrared depth binocular camera 3, a compressive strength test platform 5, and a rock abrasiveness test platform 4.

In a construction process of a TBM, a cutter head of the TBM excavates a produced rock slag 6, and a belt conveyor 7 conveys the rock slag 6 out of a tunnel. The aggregate apparatus 1, the mechanical gripper 2, the infrared depth binocular camera 3, and the rock abrasiveness test platform 4 are arranged on one side of the belt conveyor 7 in a conveying direction thereof.

Figure 2:
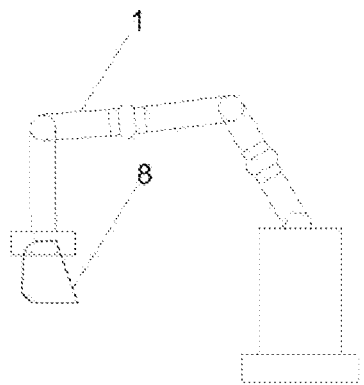
FIG. 2 is a schematic diagram of an aggregate apparatus according to Embodiment 1 of the present invention.
Figure 3:
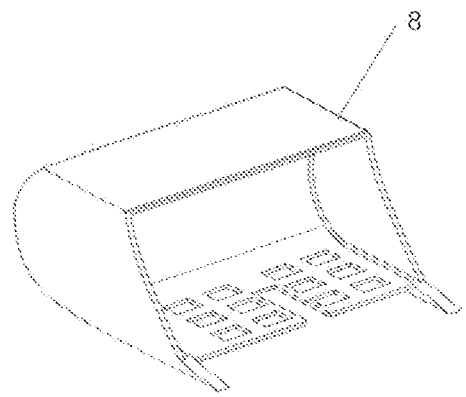
FIG. 3 is a detailed schematic diagram of a bucket according to Embodiment 1 of the present invention.

Referring to FIG. 2, the aggregate apparatus 1 includes a six-degree-of-freedom mechanical arm and a bucket 8, and may be arranged beside the belt conveyor 7 of the TBM. The mechanical arm may shift within a coordinate system in which an X axis, a Y axis, and a Z axis are perpendicular to each other, or may rotate on the three coordinate axes. The bucket 8 is connected to a distal end of the mechanical arm, and the mechanical arm controls a position and a posture of the bucket 8. Referring to FIG. 3, a bottom surface of the bucket 8 is provided with a plurality of square eyelets with a side length of 30 mm, and the middle of the bottom surface is provided with a gap with a length of 80 mm and a width of 30 mm. The aggregate apparatus 1 is configured to grip the rock slag 6 conveyed by the belt conveyor of the TBM, and filter rock slags with a relatively small size and dust out.

Figure 4:
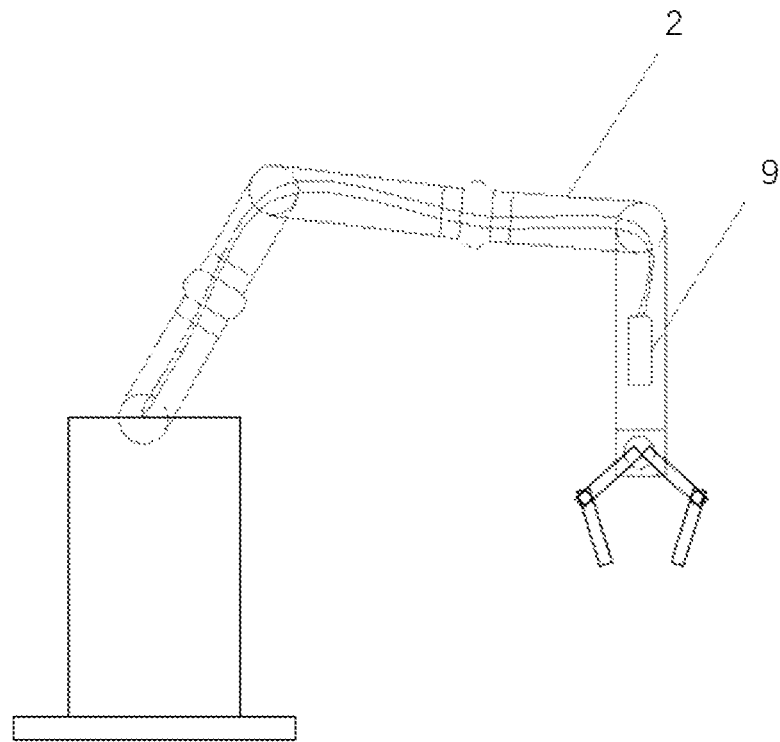
FIG. 4 is a schematic diagram of a mechanical gripper apparatus according to Embodiment 1 of the present invention.

Referring to FIG. 4, the mechanical gripper 2 includes a six-degree-of-freedom mechanical arm and a clamp, and may be arranged beside the belt conveyor 7 of the TBM. The mechanical arm may shift and rotate within a coordinate system in which an X axis, a Y axis, and a Z axis are perpendicular to each other, and a distal end thereof is connected to the clamp and controls movement of the clamp. The clamp includes four steel rods with a width no more than 20 mm, and can open and close freely and is configured to clamp a rock slag in the aggregate apparatus 1. A clamping surface of the clamp is deployed with a pressure sensor capable of locating specific position coordinates of contact points between the rock slag and the clamp.

The high-pressure sprinkler 9 is carried on the clamp, may be externally connected to a water pipe, and flushes a gripped rock slag, to remove broken slags and dust adhering to a surface of the rock slag.

The infrared depth binocular camera 3 is connected to the mechanical gripper 2, and distances between each point on the rock slag and two cameras are calculated based on a photographing result of the binocular camera for the same object (rock slag) from different angles, so as to determine a spatial position of each point on the rock slag, and thereby finally implementing three-dimensional imaging for the slag. Because the TBM has environment features such as heavy dust and heavy fog, a light ray of a common camera does not have a sufficient penetration capability. Therefore, infrared light is required, that is, a rock slag acquired by the infrared depth binocular camera 3 is used to perform photographing and three-dimensional imaging.

Because before testing a compressive strength and an abrasiveness index of the rock slag, a three-dimensional model of the rock slag needs to be obtained through calculation for processing, one of two contact points between the clamp and the rock slag is set to a zero point, which points to other point. A right-handed coordinate system is established by using a direction for the pointing as an x axis direction. Coordinates of any point on the surface of the rock slag are obtained from the coordinate system, to calculate two points with a shortest straight-line distance therebetween. A connection line between the two points is a maximum size direction of the rock slag. A distance between a middle point of the maximum size direction and any point on the surface of the rock slag is calculated, to obtain a point with a shortest distance from the middle point of the maximum size direction to the surface of the rock slag. A connection line between the middle point and the obtained point is used as a minimum size direction of the rock slag. Two intersection points between the minimum size direction and the surface of the rock slag are determined as two loading points for a compressive strength experiment.

Further, a smallest cross section in all cross sections of the rock slag in the minimum size direction is found, and an average width of the cross section is calculated with the minimum size direction as a length on the cross section and a width direction of the cross section as a vertical direction of the minimum size direction. A rock slag for a compressive strength test related to the present invention needs to meet two sample standards:

1. A spacing between loading points is longer than 30 mm but shorter than 50 mm.

2. The spacing between loading points is greater than 0.3 times the average width of the smallest cross section in the minimum size direction, and is not greater than the average width.

An infrared depth imaging model of the rock slag and important geometrical parameters thereof are obtained: relative coordinates of the loading points, the spacing between the loading points, the minimum size direction, and a width of a smallest cross section passing through the two loading points.

It should be noted that there are numerous spatial rock slag cross sections passing through a straight line of the minimum size direction, which may be analogous to all cross sections in a cylinder that pass through a straight line formed by connecting an upper circle center and a lower circle center. A width of the smallest cross section perpendicular to the minimum size direction is a length of a line segment of a straight line, on the smallest cross section and perpendicular to the minimum size direction, that is cut off by the surface of the rock slag, and an average value thereof is an average width of the smallest cross section perpendicular to the minimum size direction.

If it is determined that a rock slag under test meets a requirement, coordinate transformation is performed for the relative coordinates of the loading points, and the relative coordinates of the loading points are transformed into coordinates with the ground as a reference system. As described above, one of the contact points between the clamp and the rock slag is set to a zero point of a relative reference system of a rock slag model, and the other point is located on an x axis. Coordinates of the two contact points between the clamp and the rock slag relative to a ground reference system may be determined by using the pressure sensor on the clamp. Therefore, a mapping relationship between quantity reference systems may be established based on coordinates of the two contact points in the ground reference system and the reference system of the rock slag model, to transform relative coordinates of the loading points of the rock slag into coordinates relative to the ground reference system, so that the mechanical gripper 2 can perform displacement and rotation operations on the rock slag by using the coordinates as a reference.

For an abrasiveness test, relatively flat regions with a long axis not less than 10 mm on the surface of the rock slag need to be acquired, to ensure that a testing steel pin 12 horizontally moves at a same caved depth. Therefore, points on the established rock slag three-dimensional model need to be detected in an enumeration manner, to search for square regions with a length not less than 15 mm, a width not less than 2 mm, and a height difference within 0.5 mm. Then a movement region of the steel pin 12 is determined by using the coordinate transformation method. An arm of the clamp adjusts a direction of the slag, so that the flat regions thereof is maintained horizontal, and a direction of a long axis of the region is consistent with a movement direction of the steel pin 12.

Figure 5:
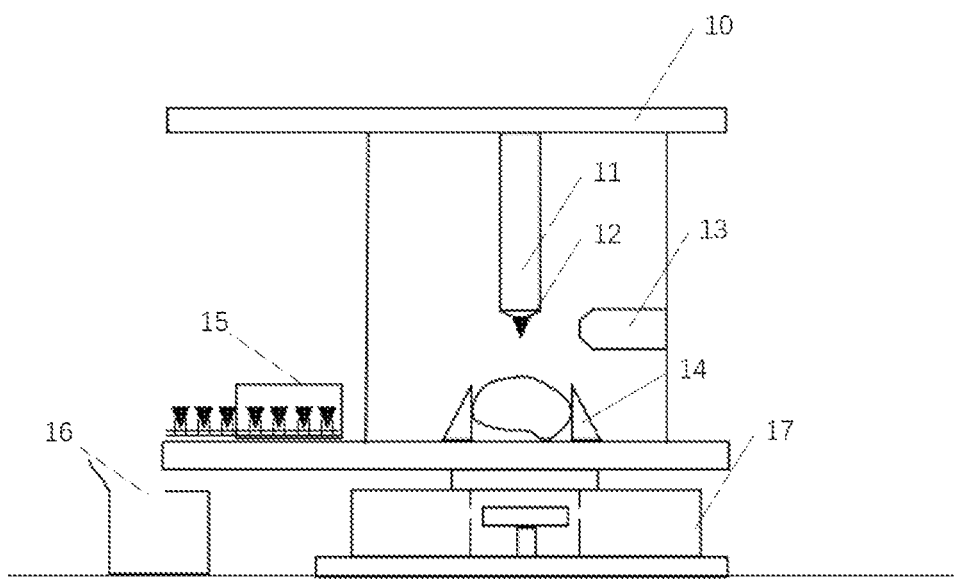
FIG. 5 is a schematic diagram of an abrasiveness index test platform according to Embodiment 1 of the present invention.

Referring to FIG. 5, a rock abrasiveness test platform includes a vibration damping base 17, a test platform support, an electric hydraulic telescopic oil cylinder 11, a slide guide rail, a rod stepping motor, a steel pin fixture, a steel pin 12, a steel pin assembly line replacement belt, a pin supply circular disk 15, an abradant steel pin collecting box 16, a CCD microscope camera 13, a rock fixture 14, and a program-controlled host 20. The vibration damping base 17 is located at a bottom portion of the rock abrasiveness test platform 4. When the TBM generates vibration due to tunneling, a piston in the vibration damping base also performs back and forth movement inside a cylinder barrel. Liquid oil inside a housing flows back and forth between two inner cavities, and friction between a hole wall and liquid oil and friction inside liquid molecules form a damping force to vibration, so that TBM vibration energy is transformed into heat energy, to be absorbed by the liquid oil and a housing of a damper. Therefore, the platform support is not interfered by TBM vibration, thereby improving test stability.

The test platform support includes an upper platform support, a test platform base, and four test platform columns supporting an entire test platform apparatus, and is a supporting framework of the test platform. The electric hydraulic telescopic oil cylinder 11 is invertedly hung on the upper platform support of the test platform, with a bottom portion of the electric hydraulic telescopic oil cylinder clamped at the slide guide rail, and is movable along the slide guide rail under drive of a sliding stepping motor. An end of the electric hydraulic telescopic oil cylinder 11 is the steel pin fixture. The hydraulic telescopic oil cylinder is connected to the program-controlled host 20, and may automatically control the fixture to move up and down within a limited range.

The slide guide rail is arranged on the upper platform support, a cross section of the guide rail is I-shaped, and a length of the slide guide rail is beyond the bottom portion of the electric hydraulic telescopic oil cylinder 11 by 50 cm. A rod of the rod stepping motor is connected to the electric hydraulic telescopic oil cylinder, so that the electric hydraulic telescopic oil cylinder can move along the slide guide rail under drive of the rod stepping motor. Precision of the rod stepping motor should achieve that the electric hydraulic telescopic oil cylinder is controlled to move along the guide rail for 10 mm per minute.

The steel pin fixture is a two-wedge fixture. Opposite surfaces of a two-wedge fixture are serrated surfaces, to increase friction during steel pin clamping. The two-wedge fixture may be controlled by a host to open or close. A cone tip of the steel pin is of 90 degrees, and the steel pin 12 includes a conic section and a cylindrical section. The conic section has a height of 1 cm, and a cone tip is of 90 degrees. The cylindrical section has a length of 5 cm, and a surface thereof is a grain surface, which can also increase friction between the surface and the steel pin fixture.

Figure 6:
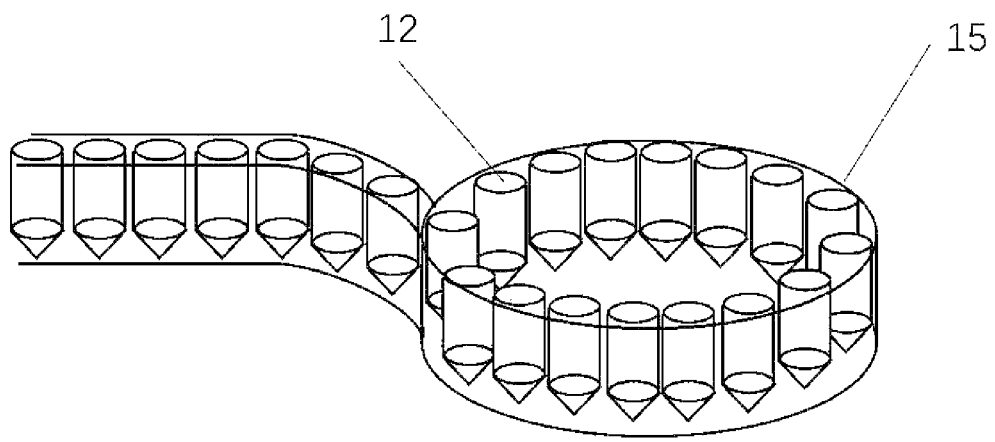
FIG. 6 is a detailed schematic diagram of a pin supply circular disk according to Embodiment 1 of the present invention.

Referring to FIG. 6, the steel pin assembly line replacement belt is located on another end relative to the guide rail of the rod stepping motor, and is configured to provide steel pins 12 for replacement. A to-be-replaced steel pin is inserted into a long chain in a form of an assembly line with a cone head downward. Each section of the chain is provided with a 90-degree upward conic groove with a cone center inward, to match the cone head of the steel pin. There are upward vertical walls of a limiting rail on two sides of the chain, and in the rail, to-be-replaced steel pins 12 move in a form of an assembly line, and are controlled by the stepping motor. There is a pin supply circular disk 15 on one side of the steel pin assembly line replacement belt, the steel pin assembly line replacement belt extends to an inner portion of the pin supply circular disk and coils inside the pin supply circular disk in concentric circles, so that a large quantity of spare steel pins 12 are capable of continuously moving out of the pin supply circular disk 15 through the assembly line replacement belt.

Further, the abradant steel pin collecting box 16 is disposed. The abradant steel pin collecting box 16 is located on the other side of the steel pin assembly line replacement belt. The limiting rail of the steel pin assembly line replacement belt is cut off at the collecting box. When moving to the collecting box, the steel pins 12 lose a limiting function of the walls of the limiting rail, and therefore fall into the collecting box. The CCD microscope camera 13 is arranged on the test platform column, and always faces a particular angle with a focus fixed.

The rock fixture 14 is located above a base, is formed by a two-wedge fixture, and can open and close to clamp a rock slag of any shape. The program-controlled host 20 is connected to electronic elements of the rock abrasiveness test platform, and controls actions of the electronic elements of the test platform, for example, a displacement of the rod stepping motor, opening and closing of the fixture, movement of the steel pin assembly line replacement belt, and an image capturing action of the CCD camera. A steel pin cone tip image captured by the CCD is processed by the program-controlled host 20, and edge information of the image is extracted by using a Canny algorithm, to obtain an edge image of a cone tip. Further, an abrasiveness index of the rock is determined by calculating a width of the cone tip.

Embodiment 2

Figure 7:
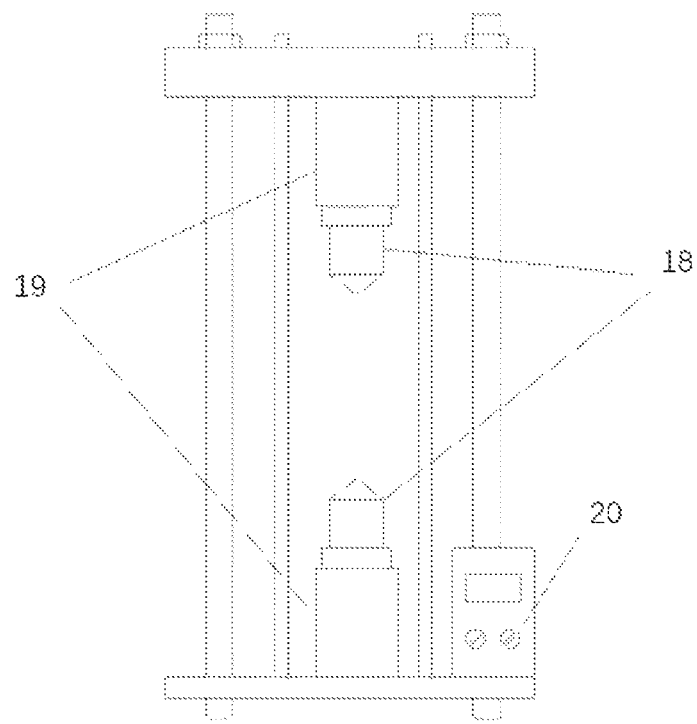
FIG. 7 is a schematic diagram of a compressive strength test platform according to Embodiment 2 of the present invention.

Based on Embodiment 1, a compressive strength test platform is added in this implementation. Referring to FIG. 7, the compressive strength test platform includes a platform support, an electric hydraulic jack 19, two loading cones 18, and a program-controlled host 20. The platform support includes an upper platform and a test platform base, and four steel columns provide support between the upper platform and a base.

The electric hydraulic jack 19 drives the two opposite loading cones 18 to shift toward each other, and after the two loading cones 18 contact a rock slag, the electric hydraulic jack 19 automatically records, by using a hydraulic sensor, a current pressure borne by the rock slag, and the pressure is transmitted to the program-controlled host 20. The two loading cones 18 are an upper movable loading cone 18 and a lower movable loading cone 18 that may shift toward each other. Cone tips of the two loading cones 18 are located on the same perpendicular line relative to the ground reference system. The program-controlled host 20 controls a displacement process of the electric hydraulic jack 19, receives a pressure borne by the rock slag from the hydraulic sensor, records a damage load when the rock slag is damaged, and determines the damage load as a compressive strength of the rock slag.

After a rock abrasiveness test is completed, the rock slag under test is clamped by the mechanical clamp to the compressive strength test platform for a compressive strength test.

Embodiment 3

Based on Embodiment 1 and Embodiment 2, this implementation discloses an automatic test method for mechanical parameters of surrounding rock applicable to a TBM, including the following working steps:

The mechanical arm of the aggregate apparatus 1 controls the bucket 8 to be in contact with a surface of the belt conveyor, and stay on the belt conveyor 7 for a short time, to shovel some rock slags moving on the belt conveyor 7. Because the shoveled rock slags have a large quantity of rock slag fragments that are less than 30 mm and do not meet a compressive strength test requirement, the bucket 8 is fold with a gap in the center of the bucket as an axis and two sides of the axis toward each other, causing a surface of the bucket to be inclined. Rock slag fragments with a particle size less than 30 mm pass through the gap of 30 mm retained in the middle of the bucket, and rock slags with a particle size greater than 30 mm are retained in the bucket 8.

Specifically, the mechanical arm of the aggregate apparatus 1 first moves to be located above the belt conveyor 7, subsequently the aggregate apparatus 1 controls the bucket 8 to be close to the belt conveyor 7, and the rock slags enter the bucket 8. The rock slags with a particle size less than 30 mm are sieved by an opening hole, and the rock slags with a particle size greater than 30 mm are shoveled into the bucket 8. The bucket 8 is in contact with the belt conveyor 7 for a short time, and after shoveling several rock slags with a particle size greater than 30 mm, the bucket 8 is lifted up, The mechanical arm of the mechanical gripper 2 controls a clamp to go deep from the gap of the bucket, to clamp a rock slag in the gap. After clamping the rock slag, the gap of the bucket is open, to provide sufficient space for the rock slag, so that the clamp can grip the rock slag out. A clamp surface of the clamp of the mechanical gripper 2 is deployed with a pressure sensor capable of obtaining positions of contact points between the rock slag and the clamp, and obtaining coordinates of the contact points between the rock slag and the clamp in the ground reference system.

To prevent dust from affecting precision of the abrasiveness test and the compressive strength test, the high-pressure sprinkler 9 flushes the rock slag, to remove floating dust on a surface.

The mechanical gripper 2 suspends a cleaned rock slag sample to a fixed position opposite to a lens of the infrared depth binocular camera 3. A focal length of the lens of the infrared depth binocular camera 3 is focused on the fixed position. Subsequently, the infrared depth binocular camera 3 starts to perform modeling for the rock slag, the mechanical gripper 2 continuously rotates the clamp, so that each surface of the rock slag can be photographed by the infrared depth binocular camera 3, and a three-dimensional model of the rock slag is established.

After the three-dimensional model of the rock slag is established, one of two contact points between the clamp and the rock slag is first set to a zero point, which points to the other point. A right-handed coordinate system is established with a direction of the pointing as an x axis direction. A distance between each two points in a set of all points of the rock slag model is calculated, to obtain two points with a longest distance therebetween on the rock slag model, and a connection line between the two points is used as a maximum size direction of the rock slag. A distance between a middle point of the maximum size direction and any point on a surface of the rock slag model is calculated, to obtain a point with a shortest distance from the middle point of the maximum size direction to the surface of the rock slag. A connection line between the middle point and the obtained point is used as a minimum size direction of the rock slag. Two intersection points between the minimum size direction and the surface of the rock slag model are determined as two loading points for the compressive strength experiment. Subsequently, areas of all cross sections of the rock slag passing through the minimum size direction are calculated, to find a smallest cross section passing through the minimum size direction. A vertical direction of the minimum size direction on the smallest cross section is defined as a width direction, and an average width of the smallest cross section is calculated.

After geometrical information features of the rock slag are obtained, whether the rock slag sample meets the foregoing two compressive strength test standards needs to be detected.

1. A spacing between loading points for the compressive strength experiment is longer than 30 mm and shorter than 50 mm.

2. The spacing between loading points for the compressive strength experiment is greater than 0.3 times the average width of the smallest cross section in the minimum size direction, and is not greater than the average width.

If the compressive strength test standards are not met, the mechanical gripper 2 places the sample back to the belt conveyor. The sample is discarded, and a new sample in the bucket is clamped. Three-dimensional points on the surface of the slag model are searched for in an enumeration manner simultaneously, to find squared regions having a length not less than 15 mm, a width not less than 2 mm, and a height difference within 0.5 mm. The mechanical gripper 2 adjusts a posture of the rock slag to be located in a horizontal direction of a relatively flat squared region obtained through searching. A direction of a long axis is consistent with a direction of the steel pin 12.

After relative coordinates of the loading points are obtained, coordinate transformation need to be performed on the relative coordinates of the loading points, and the relative coordinates of the loading points are transformed into coordinates with the ground as a reference system. As described above, one of the contact points between the clamp and the rock slag is set to a zero point of a relative reference system of a rock slag model, and the other point is located on an x axis. Coordinates of the two contact points between the clamp and the rock slag relative to a ground reference system may be determined by using the pressure sensor on the clamp. Therefore, a mapping relationship between quantity reference systems may be established based on coordinates of the two contact points in the ground reference system and the reference system of the rock slag model, to transform relative coordinates of the loading points of the rock slag into coordinates relative to the ground reference system, so that the mechanical gripper 2 can perform displacement and rotation operations on the rock slag by using the coordinates as a reference.

A spatial relationship between two coordinate systems is established based on coordinates of the contact points between the rock slag and the clamp in the ground reference system and the relative reference system inside the rock slag, so as to transform coordinates of any point on the rock slag into coordinates in the ground reference system. After obtaining the coordinates of the rock slags in the ground reference system, the mechanical gripper 2 performs fine adjustment on a position and a posture of the rock slag in the ground reference system. A coordinate transformation formula is shown in a formula below:

$$\begin{bmatrix} x \\ y \\ z \end{bmatrix} = \begin{bmatrix} \cos\varphi & 0 & -\sin\varphi \\ 0 & 1 & 0 \\ \sin\varphi & 0 & \cos\varphi \end{bmatrix} \begin{bmatrix} 1 & 0 & 0 \\ 0 & \cos\omega & -\sin\omega \\ 0 & \sin\omega & \cos\omega \end{bmatrix} \begin{bmatrix} \cos\kappa & -\sin\kappa & 0 \\ \sin\kappa & \cos\kappa & 0 \\ 0 & 0 & 1 \end{bmatrix} \begin{bmatrix} x' \\ y' \\ z' \end{bmatrix} + \begin{bmatrix} x_1 \\ y_1 \\ z_1 \end{bmatrix}$$

where x, y, z are respectively coordinates in the ground reference system, and x', y', z' are coordinates in the reference system of the rock slag. $x_1$, $y_1$, $z_1$, and $x_2$, $y_2$, $z_2$ are respectively coordinates of two contact points between the rock slag and the clamp in the ground reference system.

After a detection for the three-dimensional model of the rock slag, a clamp arm first adjusts the position and a direction angle of the rock slag, so that flat regions of the rock slag are maintained horizontal and upward, a direction of a long axis is consistent with a direction of the steel pin 12, and a point to be scratched by the steel pin 12 is located at a lower-front side of the steel pin 12. The clamp places the rock slag in the middle of the rock fixture 14 of the rock abrasiveness test platform, and enables the middle point of the maximum size direction of the rock slag to coincide with a vertical line of the center of the fixture. Subsequently, the clamp of the mechanical gripper 2 releases the rock slag, and the rock fixture 14 closes to clamp the rock slag. Subsequently, the program-controlled host 20 for the rock slag of the rock abrasiveness test platform controls the rod stepping motor to drive the electric hydraulic telescopic oil cylinder 11 to slide to an intersection point between the guide rail and the vertical line of the center of the fixture. Subsequently, the electric hydraulic telescopic oil cylinder 11 drives the steel pin fixture clamping a steel pin 12 to shift downward, until the steel pin 12 contacts the rock slag. The hydraulic sensor of the hydraulic telescopic oil cylinder detects an increased pressure caused by contacting between the steel pin 12 and the rock slag, and the pressure is further increased to 70 kN.

Keeping the pressure at 70 kN, the program-controlled host 20 starts to control, through the rod stepping motor, the hydraulic telescopic oil cylinder to move along the guide rail at a constant speed of 10 mm/min, so that the steel pin 12 continues to scratch on the surface of the rock slag. A scratching time length is 1 min, and a scratching distance is 10 mm. After the scratching is completed, the hydraulic telescopic oil cylinder lifts the steel pin 12, and lifts the steel pin 12 to a position in which a cone tip of the steel pin 12 is at the same height as the foregoing CCD microscope camera 13. A focus position of CCD microscope camera 13 is an intersection point between the vertical line of the center of the fixture and a line of sight of the camera, so that the steel pin 12 is located exactly at the cone tip of the steel pin 12, and therefore the CCD microscope camera 13 captures a high-resolution image of the cone tip of the steel pin 12.

After obtaining the high-resolution image of the cone tip, extraction on a steel cone edge in the image is performed on the image by using a Canny algorithm, and then a width of the tip of a steel cone after scratching on the surface of rock slag is calculated, and the width thereof is a determined abrasiveness the index of the rock.

After the abrasiveness test is completed, the hydraulic telescopic oil cylinder slides to be located in an upper-front side of the steel pin assembly line replacement belt, and shifts downward, to insert the abradant steel pin 12 into the assembly line replacement belt. Then the steel pin assembly line replacement belt moves forward for a position of one steel pin 12, an unused the steel pin 12 moves forward to be located below the hydraulic telescopic oil cylinder, and the steel pin fixture clamps the unused steel pin 12, to complete a replacement action for the steel pin 12. The worn-out steel pin 12 moves forward to an end of the wall of the limiting rail without the assembly line replacement belt, and then passingly falls into the abradant steel pin collecting box 16.

In some other embodiments, when completing the abrasiveness test, the mechanical gripper 2 grips the rock slag again, and adjusts the posture of the rock slag, so that the connection line between the two loading points is perpendicular to the ground. Subsequently, the mechanical gripper 2 places the rock slag on a middle point of a connection line between cone tips of the two movable loading cone 18 on the compressive strength test platform, so that a middle point between the two loading points and the middle point of the connection line between the cone tips coincide with each other, and thereby being ready for the compressive strength test.

The movable loading cones 18 of the compressive strength test platform simultaneously shift toward each other under the drive of the electric hydraulic jack 19, until the two loading cones 18 contact the rock slag and starts to apply a load. After a certain load is applied to the rock slag, the rock slag may be fixed between the two cones. In this case, the mechanical gripper 2 can leave the rock slag and grip a to-be-gripped rock slag on the aggregate apparatus 1 instead, thereby forming an assembly line operation mode. As a pressure of the hydraulic jack continues to increase, the rock slag is damaged under an action of a concentrated load. In this case, the program-controlled host 20 records the pressure of the hydraulic jack, to calculate a compressive strength value of the rock slag sample.

Specifically, a geometric size of the rock slag model is automatically analyzed based on the rock slag clamped by the mechanical gripper 2. In a reference system with two contact points between the rock slag and the mechanical gripper 2 as coordinate axes, relative coordinates of the rock slag of two loading points of the rock slag, a width of a smallest cross section of the rock slag, and a spacing between loading surfaces of the rock slag are calculated. Based on the relative coordinates and absolute coordinates of the two loading points, a relative coordinate system of the rock slag is associated with the ground reference system by using a coordinate transformation formula. The rock slag is rotated and shifted according to a position of a minimum size point of the rock slag, so that the minimum size point of the rock slag and the two loading cones 18 are controlled on a straight line perpendicular to the ground. Angles at which the clamp needs to rotate in directions x, y, and z are respectively φ, ω, and κ, which are calculated according to the following formulas:

$$\varphi = \arccos\left(\frac{x_2 - x_1}{\sqrt{(x_2 - x_1)^2 + (y_2 - y_1)^2 + (z_2 - z_1)^2}}\right)$$

$$\omega = \arccos\left(\frac{y_2 - y_1}{\sqrt{(x_2 - x_1)^2 + (y_2 - y_1)^2 + (z_2 - z_1)^2}}\right)$$

$$\kappa = \arccos\left(\frac{z_2 - z_1}{\sqrt{(x_2 - x_1)^2 + (y_2 - y_1)^2 + (z_2 - z_1)^2}}\right)$$

Further, the mechanical gripper 2 aligns the loading points with the two cone tips of the loading cones 18 of the compressive strength test platform based on the coordinates of the loading points in the ground reference system that are obtained through conversion, and then the electric hydraulic jack 19 is started, so that the two the loading cones 18 start to move towards each other until the two cone tips contact the rock slag. The hydraulic sensor inside the electric hydraulic jack 19 reads a standard for that a hydraulic pressure begins to rise and determining that the cone tips the rock slag are in contact. In this case, the mechanical gripper 2 leaves the rock slag. Then the electric hydraulic jack 19 continues to pressurize until the rock slag is damaged and automatically records a damage load. An equivalent rock compressive strength is calculated according to the follow formula:

$$I_s = \frac{P}{D_e^2}$$

where $I_s$ is an uncorrected rock point load strength (Mpa); P is the damage load (N), $D_e$ is an equivalent rock core diameter (mm), and the equivalent core diameter $D_e$ is calculated according to the following formula:

$$D_e^2 = \frac{4WD}{\pi}$$

where D is the spacing between the loading points, and W is an average width of the smallest cross section passing through the minimum size direction.

The specific implementations of the present invention are described above with reference to the accompanying drawings, but are not intended to limit the protection scope of the present invention. A person skilled in the art should understand that various modifications or deformations may be made without creative efforts based on the technical solutions of the present invention, and such modifications or deformations shall fall within the protection scope of the present invention.

What is claimed is:

1. An automatic test system for mechanical parameters of surrounding rock applicable to a TBM, comprising:
    an aggregate portion, capable of collecting a rock slag in a TBM tunneling process in real time;
    a gripping portion, capable of gripping any rock slag from obtained rock slags;
    a visual processing apparatus, capable of: performing three-dimensional imaging for a rock slag under test in an infrared ranging manner; calculating positions of loading points for an abrasiveness test experiment, and determining, based on a spacing between the loading points, whether the rock slag under test meets a requirement; and determining actual positions of the loading points if the rock slag under test meets the requirement, and determining a region, on a surface of the rock slag, that meets a set condition as an action region for the abrasiveness test experiment; and
    a rock abrasiveness test apparatus, capable of automatically performing an abrasiveness test for a rock slag under test that meets a requirement.

2. The automatic test system for mechanical parameters of surrounding rock applicable to a TBM according to claim 1, further comprising: a compressive strength test apparatus, capable of automatically performing a compressive strength test on the rock slag under test after the abrasiveness test.

3. The automatic test system for mechanical parameters of surrounding rock applicable to a TBM according to claim 2, wherein the compressive strength test apparatus comprises:
    a bearing support, a movable loading cone disposed on one end of the bearing support, a fixed loading cone disposed on the other end of the bearing support, and a driving apparatus configured to drive the movable loading cone to move, wherein a hydraulic sensor is disposed on the driving apparatus and connected to a program-controlled host, the hydraulic sensor transmits a detected pressure provided by the driving apparatus to the program-controlled host, the program-controlled host controls a pressurization process of the driving apparatus, records pressure data, and uploads the pressure data to a TBM control terminal.

4. The automatic test system for mechanical parameters of surrounding rock applicable to a TBM according to claim 1, wherein the aggregate portion comprises a robot body and a first mechanical arm disposed on the robot body, and a distal end of the first mechanical arm is provided with a mechanical bucket that is capable of moving freely and that is configured to shovel several rock slags in a TBM tunneling process.

5. The automatic test system for mechanical parameters of surrounding rock applicable to a TBM according to claim 4, wherein a screen mesh of a set size is disposed on a bottom surface of the mechanical bucket.

6. The automatic test system for mechanical parameters of surrounding rock applicable to a TBM according to claim 4, wherein the gripping portion comprises a second mechanical arm disposed on the robot body; and a distal end of the second mechanical arm is provided with a mechanical clamp that is capable of moving freely and that is configured to clamp any rock slag from the mechanical bucket.

7. The automatic test system for mechanical parameters of surrounding rock applicable to a TBM according to claim 6, wherein a clamp surface of the mechanical clamp is provided with a pressure sensor capable of locating absolute coordinates of contact points between the clamp and a rock slag.

8. The automatic test system for mechanical parameters of surrounding rock applicable to a TBM according to claim 6, wherein a high-pressure sprinkler is disposed on the mechanical clamp, and the high-pressure sprinkler is externally connected to a water pipe, and capable of flushing a gripped rock slag.

9. The automatic test system for mechanical parameters of surrounding rock applicable to a TBM according to claim 1, wherein the visual processing apparatus sets a coordinate system according to contact points between a clamp and the rock slag under test; determines two points with a longest straight-line distance therebetween on a surface of the rock slag according to coordinates of points on the surface of the rock slag, wherein a connection line between the two points is a maximum size direction of the rock slag; calculates a distance between a middle point of the maximum size direction and any point on the surface of the rock slag, to obtain a point with a shortest distance from the middle point of the maximum size direction to the surface of the rock slag, wherein a connection line between the middle point and the obtained point is used as a minimum size direction of the rock slag; and determines two intersection points between the minimum size direction and the surface of the rock slag as two loading points for a compressive strength experiment.

10. The automatic test system for mechanical parameters of surrounding rock applicable to a TBM according to claim 9, wherein a smallest cross section in all cross sections of the rock slag in the minimum size direction of the rock slag is found, and an average width of the cross section is calculated with the minimum size direction as a length on the cross section and a width direction of the cross section as a vertical direction of the minimum size direction; and if a spacing h between the two loading points meets: A≤h≤B, and k* average width of cross section ≤h≤average width of cross section, wherein 0<k<1 and A and B are set values, it is determined that the rock slag under test meets the requirement.

11. The automatic test system for mechanical parameters of surrounding rock applicable to a TBM according to claim 1, wherein the rock abrasiveness test apparatus comprises a vibration damping base and an test platform support disposed on the vibration damping base, a rock slag bearing portion and a scalable member disposed opposite to the bearing portion are disposed on the test platform support, and the scalable member is scalable under drive of the driving apparatus; a steel pin fixture configured to clamp a steel pin is disposed on a top of the scalable member; the scalable member is movable along a guide rail disposed in a direction parallel to the action region for the abrasiveness test experiment on the rock slag; and an image acquisition apparatus is further disposed on the test platform support, and an image of the steel pin after an action with the rock slag is obtained and processed by using the image acquisition apparatus, to determine a rock abrasiveness index.

12. The automatic test system for mechanical parameters of surrounding rock applicable to a TBM according to claim 11, wherein the rock abrasiveness test apparatus further comprises a steel pin assembly line replacement belt, there is a pin supply circular disk on one side of the steel pin assembly line replacement belt, the steel pin assembly line replacement belt extends to an inner portion of the pin supply circular disk and coils inside the pin supply circular disk in concentric circles, so that a large quantity of spare steel pins are capable of continuously moving out of the pin supply circular disk through the assembly line replacement belt; and further, the steel pin assembly line replacement belt is in a form of a long chain, each section of the chain is provided with a groove matching with a shape of a steel pin, there are upward vertical walls of a limiting rail on two sides of the chain, and to-be-replaced steel pins move in a form of an assembly line in the limiting rail.

13. An automatic test method for mechanical parameters of surrounding rock applicable to a TBM, based on the automatic test system for mechanical parameters of surrounding rock applicable to a TBM according to claim 1, the method comprising:

obtaining a rock slag in a TBM tunneling process as a rock slag under test;

determining a three-dimensional shape model of the rock slag in an infrared ranging manner;

calculating positions of loading points by using the three-dimensional shape model of the rock slag, and determining, based on a spacing between the loading points, whether the rock slag under test meets a requirement;

determining actual positions of the loading points if the rock slag under test meets the requirement, and selecting a region, on a surface of the rock slag, that meets a set condition as an action region for an abrasiveness test experiment, to perform an abrasiveness test; otherwise, reselecting a rock slag; and moving the rock slag under test to a set position for a compressive strength test after the abrasiveness test.

\* \* \* \* \*